United States Patent [19]

Koester et al.

[11] Patent Number: 4,923,901

[45] Date of Patent: May 8, 1990

[54] MEMBRANES WITH BOUND OLIGONUCLEOTIDES AND PEPTIDES

[75] Inventors: Hubert Koester, Concord; James M. Coull, Acton, both of Mass.

[73] Assignee: Millipore Corporation, Bedford, Mass.

[21] Appl. No.: 93,011

[22] Filed: Sep. 4, 1987

[51] Int. Cl.$^5$ ............................................. C08G 18/14
[52] U.S. Cl. .................................. 521/53; 428/305.5; 536/22; 536/23; 536/24; 536/27; 536/28; 536/29; 562/553; 562/561
[58] Field of Search ...................... 521/53; 536/22, 23, 536/24, 27, 28, 29; 562/553, 561; 428/305.5

[56] References Cited

U.S. PATENT DOCUMENTS

| | | | |
|---|---|---|---|
| 4,415,732 | 11/1983 | Caruthers et al. | 536/27 |
| 4,458,066 | 7/1984 | Caruthers et al. | 536/27 |
| 4,500,707 | 2/1985 | Caruthers et al. | 536/27 |
| 4,591,614 | 5/1986 | Miller et al. | 525/54.11 |
| 4,667,025 | 5/1987 | Miyoshi et al. | 536/27 |
| 4,668,777 | 5/1987 | Caruthers et al. | 536/27 |
| 4,689,405 | 8/1987 | Frank et al. | 536/27 |

*Primary Examiner*—Maurice J. Welsh
*Attorney, Agent, or Firm*—Hamilton, Brook, Smith & Reynolds

[57] ABSTRACT

A method is provided for synthesizing oligonucleotides and peptides directly onto a membrane. The method provides a means for generating membrane affinity supports. A modified membrane for the method of direct synthesis is also provided.

42 Claims, 5 Drawing Sheets

MEMBRANES WITH BOUND OLIGONUCLEOTIDES AND PEPTIDES

BACKGROUND OF THE INVENTION

In recent years solid phase biochemistry (e.g. *Solid Phase Biochemistry—analytical and synthetic aspects*, W. H. Scouten, editor, John Wiley & Sons, New York, 1983) has found wide application in biotechnology. Major interests have focussed on affinity chromatography (e.g. *Affinity Chromatography—a practical approach*, editors P. D. G. Dean, W. S. Johnson & F. A. Middle, IRL Press Ltd., Oxford, 1986), *Nucleic Acid Hybridization—a practical approach*, editors B. D. Hames & S. J. Higgins, IRL Press Ltd., Oxford, 1987), immobilized enzymes and cells (e.g. *Immobilized Cells and Enzymes—a practical approach*, editor J. Woodward, IRL Press, Oxford, 1985), solid phase peptide (e.g. G. Barany & R. B. Merrifield in 'The Peptides', Vol. 2; editors: E. Gross & J. Meienhofer, Academic Press, New York, 1979) and oligonucleotide synthesis (e.g. *Oligonucleotide Synthesis—a practical approach*, editor M. J. Gait, IRL Press Ltd., Oxford, 1984). In almost all cases as given in the references cited above the nucleic acids or peptides/proteins are either adsorbed or non-specifically linked to beaded material such as cellulose, glass beads, Sephadex, Sepharose, agarose, polyacrylamide, porous particulate alumina, hydroxyalkyl methacrylate gels, diol-bonded silica or porous ceramics. Flat material such as filter disc of nylon and nitrocellulose are very frequently used to immobilize nucleic acids for hybridization experiments by adsorption. In some applications in this area chemically modified paper is employed; cellulose is either functionalized with a diazobenzyloxymethyl (J. C. Alwine et al. in *Methods in Enzymology*, Vol. 68, editor: R. Wu, Academic Press, New York and London, page 220, 1979) or a O-aminophenylthioether (B. Seed, *Nucleic Acids Res.* Vol. 10, page 1799, 1982) derivative, which in both cases leads to a non-specific covalent linkage of nucleic acids to the paper. In another attempt the surface of tubes made from vinylacetate-ethylene copolymers was chemically activated to furnish a non-specific covalent attachment of proteins to the tube surface (G. Manecke & H. G. Vogt, *J. Solid-phase Biochem.*, vol. 4, page 233, 1979). It should be noted that in the latter case no porous structure is available to supply a significant amount of molecules to be attached to the carrier.

Recent attention has focussed on the development of methods for the site specific covalent attachment of biomolecules to solid supports. Synthetic DNA molecules covalently bound to bead matrices such as cellulose (P. T. Gilham in *Methods in Enzymology*, editors L. Grossman & K. Moldave, vol. 21, part D, page 191, Academic Press, New York and London, 1971 and J. T. Kodanaga & R. Tjian, *Proc. Natl. Acad. Sci. USA*, Vol. 83, page 5889, 1986), glass beads of controlled porosity (T. Mizutani & Y. Tachibana, *J. Chromatogr.*, Vol. 356, page 202, 1986) and latex microspheres (J. N. Kremsky et al. *Nucleic Acids Res.* Vol. 15, page 2891, 1987) have been used for affinity purification of complementary nucleic acids and for sequence specific binding of proteins and as reactants in enzymatic ligation reactions. Likewise synthetic peptides attached to various beaded carriers, including sepharaose and agarose, have been widely used for affinity isolation of enzymes (P. Cuatrecasas, M. Wilchek & C. B. Anfinsen, *Proc. Natl. Acad. Sci. USA*, vol. 61 page 636, 1968), antibodies (E. Hurwitz et al., *Eur. J. Biochem.*, vol. 17, page 273, 1970) and other proteins (B. Penke et al., *J. Chromatogr.*, Vol. 376, page 307, 1986).

Synthesis of affinity matrices usually involves the reaction of a support bound electrophilic function with a nucleophilic group within the oligonucleotide or within the peptide. Conversely, the electrophilic function may be on the biomolecule and undergoes reaction with a nucleophilic group on the polymeric support.

More often, peptides are coupled to solid carriers via the various reactive functional groups of the amino acid side chains as well as through the amino and carboxyl termini of the biopolymer. Oligonucleotides are relatively more difficult to attach to solid supports because they do not contain any strong nucleophilic or electrophilic centers. As a result, a number of methods and reagent have been described that allow for the chemical synthesis of oligomers containing reactive functionalities at defined positions in the molecule, preferentially at one of the termini of the biopolymer (see, e.g. J. M. Coull et al., *Tetrahedron Lett.* vol. 27 page 3991, 1986; S. Agrawal et al., *Nucleic Acids Res* vol. 14, page 6227, 1986; B. A. Conolly, *Nucleic Acids Res.*, vol. 15, page 3131, 1987; B. A. Conolly and P. Rider, *Nucleic Acids Res.*, vol. 12, page 4485, 1985).

Since both approaches require the synthesis and isolation of an oligonucleotide or peptide prior to attachment to the solid matrix, a significant improvement would be the direct solid phase synthesis of the biomolecule onto the support. In this way the affinity support can be directly generated. Two prior examples of this approach include the chemical synthesis of oligo-dT on cellulose beads (P. T. Gilham, see above) for the affinity isolation of poly A tail containing mRNA and the synthesis of short peptides on polyethylene pegs useful for antibody epitope mapping by employing the specific affinities of certain amino acid sequences on the antibody to react strongly and specifically with the antigen (H. M. Geysen et al., *Proc Nat'l. Acad. Sci. USA*, vol. 82, page 3998, (1984)). Polyethylene pegs are only useful for very specific purposes and suffer from the extreme low loading of immobilized biomolecules due to the non-porous structure. In a description of a process for the simultaneous chemical synthesis of several oligonucleotides paper discs have been used (DE No. 3301833 and EP No. 114599). This material cannot be recommended to serve as affinity support, because the material apparently does not allow to use the state-of-the-art phosphoamidite chemistry for the construction of long oligonucleotides with more than one hundred nucleotide units in the sequence (N. D. Sinha et al., *Nucleic Acids Res.*, 12:4539, (1984)). With the phosphate triester method (see e.g. M. Gait as cited above) only relatively short oligonucleotides (in the range of twenty nucleotide units containing sequences) can be obtained with the paper disc method. Moreover, after a few synthetic cycles employing the necessary treatment with different reagents and washing steps the paper gets very fragile and looses its mechanical stability. No peptides have been synthesized so far on paper; it is very probable that due to the harsh conditions necessary to synthesize peptides the cellulose matrix will be disrupted. Thus, affinity supports cannot be obtained by virtue of chemical synthesis of oligonucleotides or peptides onto paper as solid support.

Nucleic acids and peptides or proteins have been immobilized onto beaded and flat polymeric supports either by adsorption or by non-specific covalent linkage. To mediate an efficient and specific interaction using hybridization or affinity techniques between the soluble and immobilized biomolecules, a specific covalent attachment of the biomolecule involving only one terminal function would be optimal. This would make available the whole sequence of the immobilzed biomolecule to interact with the complementary molecule in solution. Adsorption or non-specific covalent binding, however, involves several functions in the biomolecule, which are then rendered unavailable for the desired intermolecular interaction. Adsorption has furthermore the disadvantage that some of the immobilized biomolecules can be washed out (desorbed) during the hybridization or affinity process. This has to be particularly considered if the affinity support should be reused several times.

Whereas the terminus specific covalent attachment of oligonucleotides or peptides onto solid supports using the stepwise synthetic approach has been performed using beaded supports or paper discs (in the case of oligonucleotides) or beaded supports and polyethylene pegs (in the case of oligopeptides) no synthesis of these biopolymers has been reported employing membrane-type supports.

A membrane, a being flat and highly porous, mechanical stable material, would be most advantageous as affinity support, because it could be handled easily, cut into various sizes, stacked on top of each other for up-scaling purposes and reused several times. Furthermore, the support should be chemically stable under the conditions of oligonucleotide and peptide synthesis and should not show non-specific binding of either nucleic acids or proteins as this would give rise to a sensitivity-reducing background interaction. The development of an affinity support which fulfills these different requirements is not a trivial task. Whether the direct chemical synthesis of oligonucleotides or peptides is possible on such an insoluble support can also not be predicted. As mentioned, paper could only serve as a support for solid phase oligonucleotide synthesis when the phosphotriester approach was employed; for reasons which are still unclear, the much more efficient and state-of-the-art phosphoamidite chemistry which is very successfully used on porous glass beads did not work on paper.

SUMMARY OF THE INVENTION

This invention pertains to a method of synthesizing oligonucleotides (DNA and/or RNA fragments) or peptides covalently and specifically linked to membranes. The invention also pertains to modified membranes for synthesis of oligonucleotides and peptides and to membranes having oligonucleotides or peptides attached thereto by a terminal specific attachment (the biopolymer is covalently bound at one of its termini).

According to the method of this invention a modified membrane is employed which is represented by the formula:

$$P-X-Y-N-Z-S^W$$

wherein P represents a polymeric membrane support linked to a protected nucleoside or amino acid $S^W$, where W represents protecting groups, through a linker Y—N—Z, where N represents a spacer group and Y and Z represent the same or different functional groups, the linker being bound to the membrane through a functional group X on the membrane.

The membrane is chemically functionalized to anchor the first nucleotide or peptide building block. To minimize steric hindrance from the membrane backbone a suitable spacer function is placed between the polymer backbone and the first anchored building block. The synthesis of the specific biopolymer sequence is performed either manually or by automated synthesis. Standard chemical protocols for the stepwise construction of either oligonucleotides or peptides can be employed. After the assembly of the desired specific sequence the protecting groups can be removed to generate biologically functional molecules.

Depending on the linkage to the membrane the synthesized biopolymer can either be cleaved off for subsequent characterization and/or identification or it can be left on the membrane in an unprotected form. The latter can be used to interact with other molecules via hybridization or other reactions of specific affinity. This is of importance for the purification and detection of, e.g., nucleic acids such as mRNA, genomic DNA sequences and rRNA and for the detection of organisms and viruses as well as enzymes and antibodies.

DETAILED DESCRIPTION OF THE INVENTION

Figure 1:
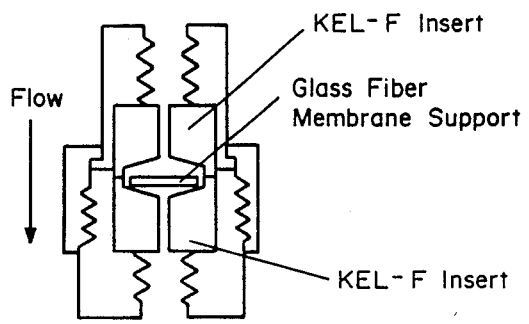
FIG. 1 shows a specially designed holder for a membrane for synthesis of an oligonucleotide or oligopeptide.

The solid support which is the starting material for the synthesis of either oligonucleotide or peptide sequences has the general formula (1)

$$P-X-Y-N-Z-S^W \qquad (1)$$

in which P is the underlying polymeric material comprising the porous membrane structure, X is a functional group on the polymeric material allowing the first synthetic building block S (a suitably protected nucleoside or amino acid) to be anchored to the membrane via the spacer N, which has two equal or different functional groups Y and Z. W represents protecting groups for the nucleoside or amino acid moiety. Although S is shown as a single initial building block, it should be understood that S can represent a dimeric, trimeric or oligomeric starting material. For example, S can comprise a protected nucleoside-nucleotide dimer. This incipient chain can then be extended by the method of this invention. In some embodiments, a second linker can be attached to S which has a functional group from which the biopolymer can be synthesized.

Membranes which can be used in the method of this invention are flat, permeable, polymeric materials of porous structure which have a functional group X (which is native to the constituent polymer or which is introduced to the membranous polymer as described below) for attachment of the first nucleotide or peptide building block. The following four types of polymers can serve to generate the affinity membranes for the purposes of this invention:

A: Copolymers which contain functional groups due to the presence of functional groups in the respective monomers, such as acrylic (or methacrylic) acid esters having a free functionality in the alcohol part of the ester function e.g. —(CH$_2$)$_n$CH$_2$—OH, —(CH$_2$)$_n$—CH(CH$_3$)—OH (n=2-10) or an active ester function such as —COOR, R being e.g. pentafluorophenyl, p-nitrophenyl, methoxymethylene or a lactone function, which directly can react with a nucleophile. Similar types of polymers can be obtained by crosslinking dialkylsilandiols or polydialkylsiloxanes, polyvinylalcohol, polyoxymethylene or polyoxyethylene with suitable crosslinking agents such as terephthaldehyde, carboxylic acid dichlorides or bisisothiocyanates.

B. Polymers in which functional groups can be introduced by chemical modifications such as cross-linked polystyrene, polysulfone containing aromatic residues, polyesters, polyamides, polycarbonates, polyvinylacetate. Polymers with aromatic residues can be modified e.g. by Friedel-Crafts acylation followed by reduction or Grignard reaction. Other types of polymers can generate free functional groups by partial hydrolytic reactions. Polyvinylidene difluoride (PVDF) can generate functional groups (double bonds) by dehydrohalogenation.

C. Chemically inert polymers such as polysulfones, polytetrafluoroethylene (Teflon ™), polyethylene, polypropylene, polyvinylidene difluroide (PVDF) can be activated by radiation e.g. with high energy UV or Cobalt-60 and the generated ions or radicals used for grafting onto the surface of the polymer, chains containing monomers with functional groups according to A and/or B.

D. Chemically inert polymers such as polysulfones, polytetrafluorethylene (Teflon ™), polyethylene, polypropylene, polyvinylidene difluoride (PVDF) can be coated with copolymers, which already do contain free functional groups (A) or easily transformed to generate functional groups by using conventional chemical or physico-chemical processes (B,C). Another subtype could be obtained by crosslinking e.g. polyvinylalcohol on the surface of the aforementioned polymers, generating diradicals by reacting the cis-diol structure with Cer(IV)nitrate and use the radicals to start a grafting process involving monomers according to A and/or B.

Y—N—Z is a bifunctional group, in which Y reacts with the functional group X on the polymer and mediates via Z linkage to the first synthetic building block either a suitably protected nucleoside or amino acid derivative. N is a spacer group. Any suitable spacer group can be used. Substituted or unsubstituted alkyl, aryl, aryl alkyl groups are suitable. For example, N can be a variable spacer consisting of n CH$_2$ groups, n varying between 1 and 20. Spacing can also be accomplished by chains such as oligoglycine or —NH—(CH$_2$)$_m$—NHCO—(CH$_2$)$_m$—CO, m being, for example, 1 to 6. Y and Z can be the same or different and selected from a variety of standard functional groups, such as:

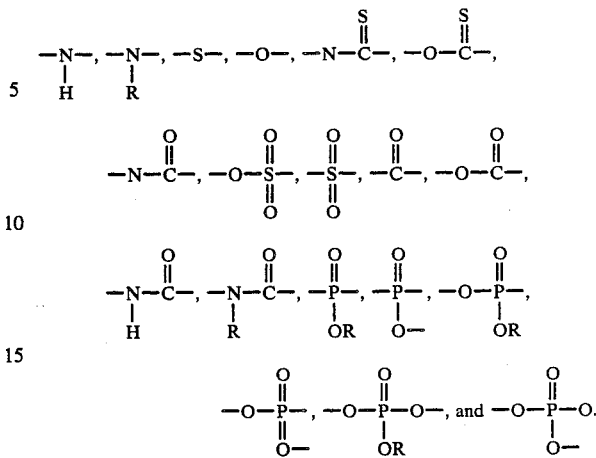

wherein R is alkyl, aryl, aralkyl, or cycloalkyl.

S represents a suitably protected first building block anchored to the membrane support P such as a nucleoside or an amino acid. The nucleoside is represented by the formula:

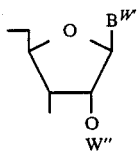

wherein W″ is H or a suitable hydroxy protecting group such as trityl groups, acyl groups or silyl groups. B is a nucleoside base such as adenine, guanine, cytosine, thymine, uracil or analogs of these bases. For example W′ can represent a baselabile acyl group generally used for protection of exocyclic amino groups on the heterocyclic nucleoside bases. The nucleoside is generally attached to the membrane via the 3′ position but can be attached at the 5′ position. When attached to the membrane that the 3′ position, the 5′ carbon can contain a protected hydroxy group. Preferred protecting groups for the 5′ hydroxy group are 4,4′-dimethyoxytrityl or 4,4′,4″-trimethyoxytrityl groups.

The amino acid building block is represented by the formula:

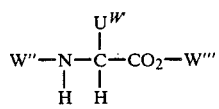

which is attached via its carboxy or amino function to the linker functional group Z. U represents an amino acid side chain, for example, naturally occurring amino acid side chains or modified versions thereof. As amino acid building blocks either the L- or rare D- or modified amino acids such as beta—or N-methyl amino acids can be linked to the membrane. W′ represents a side chain protecting group(s). When the amino acid is attached to the spacer via its carboxy function, W″ represents a protecting group for the primary amino function such as fluorenylmethoxycarbonyl or t-butyloxycarbonyl. W‴ represents a protecting group for the carboxy group such as a pentafluorophenyl group.

The affinity membrane of formula (1) is used as a solid support for the synthesis of specific and biologically relevant oligonucleotide or peptide sequences. The method of this invention yields membranes having biopolymers attached by terminal specific attachment (attached through one of the termini of the biopolymer). In general, the membranes with bound biopolymer are represented by the formula:

wherein n represents the number of nucleotide or amino acid units in the polymer (a number which is limited only by the capabilities of the synthetic chemistry employed). As discussed more fully below, the biopolymers can be left on the membrane in protected or partly protected form or they can be fully deprotected to yield the natural form of the polymer. Membranes containing deprotected biopolymers can be represented by the formula:

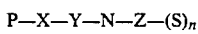

where P, X, Y, N, Z and n are as defined above and S represents a deprotected nucleotide or amino acid unit of the polymer.

The syntheses of biopolymer on the modified membrane of formula (1) can be performed either manually or in an automated synthesizer. A device such as described in FIG. 1 can be used as a membrane holder for either manual or automated syntheses. It allows for a rapid flow-through of solvents and reagents and due to high diffusion rates results in rapid and quantitative reactions. This device also demonstrates the ease of handling of membrane-type material, the advantage of this synthetic process for generation of, also for their subsequent use as, affinity supports.

To illustrate the method of this invention, Immobilon affinity membrane (IAM, 2; Millipore Corp., Bedford, Mass., USA) containing reactive electrophilic functional groups was treated with 1,2-diaminoethane (3, n=2) or 1,6-diaminohexane (3, n=6) resulting in aminoalkyl-IAM 4 (n=2 or 6) as shown in scheme I.

Synthesis of oligonucleotides:

The first nucleoside building block is usually linked to the membrane via its 3'-OH function, although linkage via the 5'-OH function may also be employed. Scheme II shows the attachment of a deoxynucleoside building block 5 to the aminoalkyl-IAM 4 via the 3'-OH function using a method known in the art to form a membrane to which a nucleoside building block is specifically and covalently linked (6). A suitably protected ribonucleoside building block can be linked to the membrane in essentially the same manner. Other methods known in the art can be employed to effect the covalent anchoring of nucleosides to a solid support and construction of oligonucleotides.

The phosphoamidite method for the synthesis of the oligonucleotide on the membrane support is outlined below. It comprises the steps of:

(a) employing proton or Lewis acids to remove the 4,4-dimethoxytrityl (DMT) protecting group;

(b) coupling a 5'-DMT- and N-protected 3'phosphoamidite after activation with a suitable activator such as tetrazole or 4-nitrophenyltetrazole to the free 5'-OH group of the membrane-bound deoxynucleoside;

(c) capping non-reacted 5'-OH groups of the immobilized deoxynucleoside (or oligonucleotide) with reagents such as acetic acid anhydride/N,N-dimethylaminopyridine, thereby reducing the occurrence of failure sequences; and (d) oxidizing the trivalent phosphite triester bond with reagents such as iodine/ 2,6-lutidine/water to the pentavalent phosphate triester bond.

Between the different reaction steps of the elongation cycle appropriate washing steps are employed. Steps (a) through (d) are repeated using in step (b) the correct building block until the desired oligonucleotide sequence is generated.

In the preferred mode the beta-cyanoethyl phosphoramidite chemistry is employed. See Sinha et al., *Nucleic Acids Res.* 12:4539 (1984). See also, U.S. patent application No. 752,178 filed June 18, 1985, the teachings of which are incorporated by reference herein. This techniques comprises coupling a nucleoside beta-cyanoethyl protected phosphoramidite to the membrane-bound nucleoside to produce a membrane-bound nucleoside-nucleotide having a phosphite triester, oxidizing the phosphite triester to form a phosphate triester linkage and sequentially coupling additional nucleoside beta-cyanoethyl protected phosphoramidites to the membrane-bound nucleoside-nucleotide and after each coupling step, oxidizing the resulting phosphite triester linkage to produce a membrane-bound polynucleotide.

To use the oligonucleotide-membrane as an affinity support for hybridization experiments the N-protecting groups of the nucleoside bases must be removed to enable Watson-Crick base pairing. Usually the phosphate protecting group (e.g. beta-cyanoethyl) is also removed to generate the naturally occuring internucleotidic linkage (phosphodiester bond). It may be of advantage, however, to keep the phosphate protecting groups. In some cases (e.g. when synthesizing the unnatural oligomethyl-phosphonate diesters) the internucleotidic linkage remains 'protected'. The synthesized oligonucleotide can also be cleaved from the membrane. It depends on the selection of X—Y—N—Z functions (formula 1) and the choice of phosphate and N-protecting groups (and 2'-OH protecting groups in the case of oligoribonucleotide synthesis) whether the oligonucleotide remains linked to the membrane (as necessary if the membrane is to serve as an affinity support) or is cleaved off the carrier during or after deprotection. It is an advantageous feature of this invention that out of the large selection of protecting groups known in the art a selection can be made which allows (by employing different sets of conditions) the oligonucleotide either to be cleaved off the membrane or to be left on the membrane after appropriate deprotection to allow hybridization on the membrane. In some cases a sequence specific optimization process should be worked out to generate high yields and a homogeneous product; for this optimization process it is necessary to identify and to characterize the oligomeric product. Once the optimal conditions have been worked out the affinity support is generated by removing only those protecting groups necessary to allow the affinity process to take place.

Peptide synthesis:

In state-of-the-art peptide synthesis, prior to anchoring the first amino acid building block to the solid support, the unnatural amino acid norleucine and a special linker molecule are attached to the solid support. The norleucine residue acts as an internal standard for the subsequent amino acid analysis of the synthesized oligopeptide; the linker molecule provides a benzyl alcohol function to esterify the first amino acid building block to the solid support. Various linker molecules are in use, which differ in reactivity of the ester linkage (see e.g., R. L. Sheppard & B. J. Williams, *Int. J. Peptide & Protein Res.*, vol. 20, page 451, 1982).

Scheme III describes the preparation of Immobilon affinity membrane IAM 4 (n=2) for the synthesis of peptides. First 4 is reacted with the active, pentafluorophenyl (Pfp) ester of norleucine 7, which is protected at the primary amino function with the fluorenylmethoxycarbonyl (Fmoc) group to furnish 8. Remaining amino groups of 4 are capped with acetic acid anhydride (step a of scheme III) and thereafter the Fmoc group is removed by treatment with 20% piperidine in N,N-dimethylformamide (step b of scheme III) resulting in the formation of 9. The primary amino group of 9 is then reacted with the pentafluoropheyl ester of the linker molecule 10 yielding the membrane derivative 11 ready for esterification to the first amino acid building block via its carboxyl terminus. The selection of p-hydroxymethylphenoxyacetic acid as linkage agent provides for an acid labile linkage to the synthesized peptide sequence. The first amino acid building block 12 is coupled to 11 via its symmetrical anydride in the presence of N,N-dimethylaminopyridine as catalyst to generate the membrane derivative 13, which now carries a covalently and specifically attached protected amino acid derivative.

In one embodiment of the method of this invention, Fmoc-protected amino acid pentafluorophenyl esters are used employing 1-hydroxybenzotriazole (HOBT) as activator. One elongation cycle is comprised of the following steps:

(a) removing the Fmoc protecting group of 13 by treatment with 20% piperidine in N,N-dimethylformamide (DMF);

(b) coupling an Fmoc protected amino acid Pfp ester to the primary amino function on the membrane using 1-hydroxybenzotriazole (HOBT) as activator to generate the first peptide bond; and (c) capping the unreacted primary aminofunctions by treatment with acetic acid anhydride.

Steps (a) to (c) are repeated by selecting the correct protected amino acid derivatives until the last building block is linked to the chain to generate the desired sequence. Step (c) is optional.

To prepare the membrane for affinity experiments the protecting groups in particular the side chain protecting groups must be removed. Depending on the selection of side chain protecting groups and linking agent, the peptide can remain on the membrane or can be removed from the membrane for identification and characterization purposes. This feature of the method is of particular importance for the generation of affinity membranes bearing peptide sequences. It is known to those skilled in the art that sequence specific problems in synthesis can occur, which make necessary an individual optimization process.

By the selection of other linking functions for attaching to the membrane known to those skilled in the art other methods of peptide synthesis can be employed (see e.g., Barany & Merrifield as cited above). Such other chemistries involve different protecting groups for the primary amino function (e.g. t-butyloxycarbonyl, tBOC), different side chain protecting groups and different coupling procedures such as the use of symmetrical amino acid anydrides or other active ester functions or activators.

The invention is illustrated further by the following examples.

EXAMPLE 1

Functionalization of Immobilon affinity membrane with alkyldiamines

Five sheets (12.5×10 cm) of Immobilon affinity membrane (IAM, 2 in scheme I) as available from Millipore Corp., Bedford, Mass. USA were placed in a dish and covered with 100 ml of 0.2 M 1,2-diaminoethane, or 1,6-diaminohexane in N,N-dimethylformamide (DMF). The reaction was allowed to proceed for 2.0 hours at room temperature with occasional agitation. After washing with anydrous methanol the membrane sheets were dried under vacuum. Picric acid binding assays showed that 4 (n=2), and 4 (n=6), contained 0.109 and 0.040 mmol of amino groups per gram of dry membrane, respectively. Picric acid binding assays were performed by accurately weighing out a piece of membrane (5 mg) and treating it with a 0.2 M solution of picric acid in dichloromethane. The membrane fragment was washed with dichloromethane and taken up in 10.0 ml of freshly prepared 4% triethylamine in dichloromethane. The absorbance of triethylammonium picrate was immediately recorded at 358 nm ($\epsilon_{358}=14,500$).

EXAMPLE 2

Attachment of protected nucleoside to IAM 4

Functionalized IAM 4 (n=6), 0.98 g (0.039 mmol of amino groups), was treated with p-nitrophenylester of N-4-benzoyl-3'-O-succinyl-5'O-dimethoxytrityldeoxycytidine (0.2 mmol), triethylamine (0.2 mmol) and 4-dimethylaminopyridine (0.5 mg) in 0.4 mL of dry DMF. After 16 hours at 20° C. the membrane was washed with methanol and dried under vacuum. Excess amino groups were acylated by exposure of material to 4.0 mL of pyridine/acetic acid anhydride, 3/1 (v/v), for 2.0 hours at 20° C. The membrane was washed with methanol and dried. A small portion (5 mg) of the support 6 (scheme II) was assayed for the presence of the dimethoxytrityl group ($\epsilon_{498}=74,500$ in 70% perchloric acid/ethanol, 1/1 (v/v). The assay indioated 0.032 mmol of nucleoside bound per gram of dry membrane 6, 80% yield.

EXAMPLE 3

Synthesis of
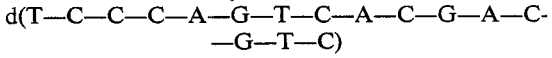
d(T—C—C—C—A—G—T—C—A—C—G—A—C—G—T—C)

Figure 2:
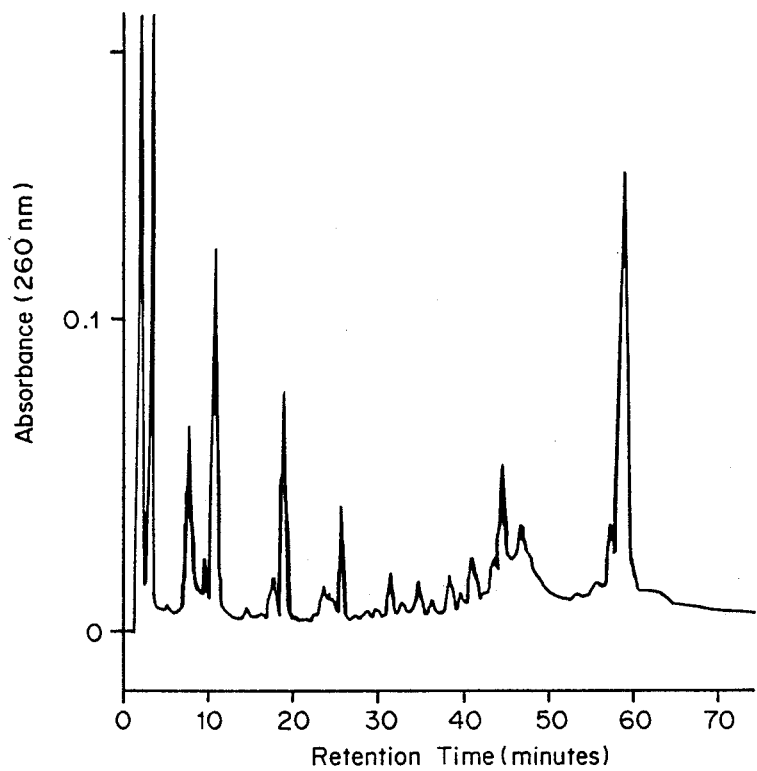
FIG. 2 shows an hplc chromatogram of the hexadecameric oligonucleotide.
Figure 3A:
FIG. 3A shows PAGE analysis of a hexadecamer oligonucleotide synthesized by the method of the invention.
Figure 3B:
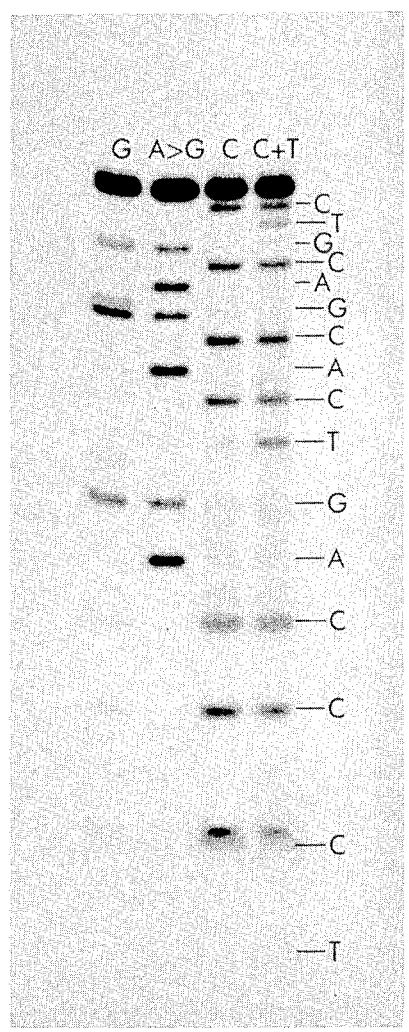
FIG. 3B shows the sequencing gel for the hexadecameric oligonucleotide.

A 0.8 cm² disc of the membrane 6 (B=cytosine, W=benzoyl) was placed in a specifically designed holder (FIG. 1) and fitted into a MilliGen 6500 automated DNA synthesizer. The above sequence was assembled automatically by using β-cyanoethylphosphoamidites (N. D. Sinha et al., as cited above) and a standard synthetic protocol. Following the last addition cycle the membrane disc was treated in a sealed tube with 0.3 mL of conc. aqueous ammonia for 12 hours at 55 C. The ammoniacal solution was concentrated and chromatographed by reverse phase hplc. The hplc chromatogram is shown in FIG. 2. The product peak was analyzed by polyacrylamide gelelectrophoresis (as described in N. D. Sinha et al.) The result is shown in FIG. 3a. The material in the main band was subjected to sequence analysis using the Maxam & Gilbert procedure (as described in N. D. Sinha et al., is cited above). The result is shown in FIG. 3b demonstrating the correctness of the synthesized hexadecamer sequence.

EXAMPLE 4

Attachment of norleucine to IAM 4

Immobilon affinity membrane 4 (n=2, scheme I), 3.20 g (0.349 mmol of amino groups), was reacted with N—Fmoc—Nle—O—Pfp (6.0 mmol) in the presence of 1-hydroxybenzotriazole (6.0 mmole) in 20 mL of dry DMF for 2.0 hours at room temperature. The support was washed with methanol, dried, and then treated for an additional 2.0 hours at room temperature, with 40 mL pyridine/acetic acid anhydride, 3/1 (v/v). The acylation reaction was terminated by washing the membrane with methanol. The amount of incorporated norleucine was 0.093 mmol/g membrane as determined by quantitation of the fluorenylmethyloxycarbonyl moiety. The assay is performed by carefully weighing in 5.0 mg of the membrane 8 (scheme III) and treatment with 0.4 mL of a mixture of piperidine and 0.4 mL dichloromethane for 30 minutes at room temperature. The solution was diluted to 10.0 mL with dichloromethane and the absorbance at 301 nm determined ($\epsilon_{301}$=7,800 for N-fluorenylmethyl piperidine in dichloromethane).

EXAMPLE 5

Attachment of the linker moiety 10 to H—Nle—IAM 9

Membrane 9, 3.2 g (0.30 mmol of amino groups) was placed in a dish containing 50 ml of 20% piperidine in dimethylformamide. After 10 minutes at 20° C., the membrane was washed 10 times with small portions of dry dimethylformamide. The wet material was then treated with 6.0 mmol of 4-hydroxymethyl phenyl acetic acid pentafluorophenyl ester and 6.0 mmol of 1-hydroxybenzotrizole in 20 ml of dimethylformamide of 2 hrs at 20° C. The reaction was terminated by washing the support sequentially with dimethylformamide, dichloromethane and methanol. Following drying, a picric acid binding assay revealed 0.002 mmol per gram of membrane of remaining amino groups, which indicates a yield of 98%.

EXAMPLE 6

Attachment of Fmoc—L—Val to IAM derivation 11

N-Fluorenylmethoxycarbonyl valine (0.46 mmol) was dissolved in 15 mL of dichloromethane and dicyclohexylcarbodiimide (0.23 mmol) was added. After 15 minutes at room temperature, dicyclohexyl urea was removed by filtration and the solution was concentrated. The residue was dissolved in 4.0 mL of dry DMF containing 4-dimethylaminopyridine (0.07 mmol) and the mixture was applied to 0.7 g of the IAM derivation 11 (scheme III), i.e. 0.085 mmol of support bound benzyl alcohol. The reaction was kept overnight at room temperature. The membrane was washed with DMF, dichloromethane and dried. As judged by release of N-fluorenylmethylpiperidine the support contained 0.07 mmol of valine per gram of dry membrane (75% yield with respect to IAM 11).

EXAMPLE 7

Synthesis of H—Ala—Asn—Lys—Gly—Phe—Leu—Glu—Glu—Val—OH.

Figure 4:
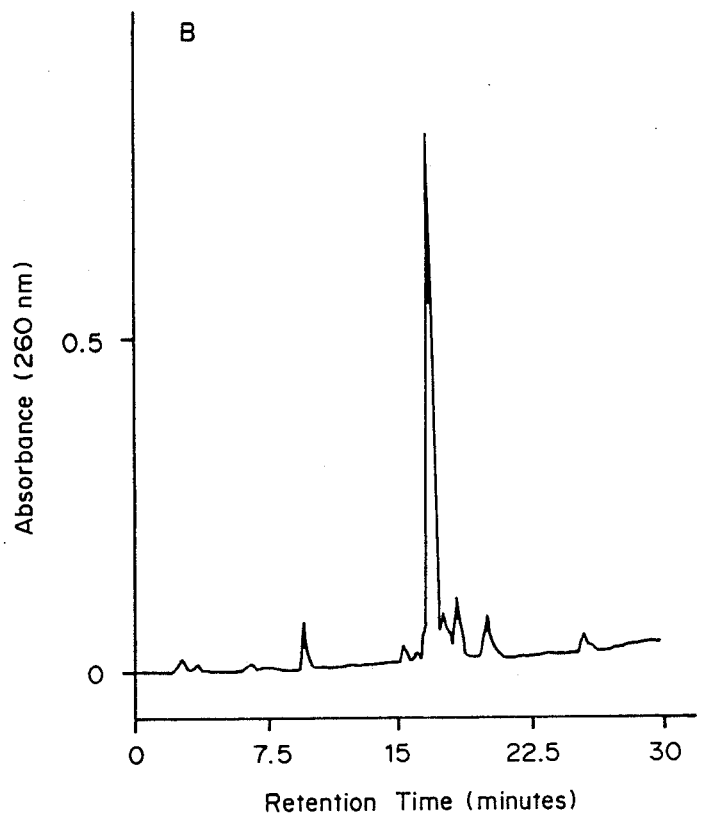
FIG. 4 shows an hplc chromatogram of a nonapeptide synthesized by the method of the invention.

An 8.0 cm² disc of valine esterified support (example 6) was placed in the bottom of a sintered glass funnel. The membrane was washed with DMF and treated with 20% piperidine in DMF for 5 minutes to remove the N-Fmoc group. Following washing with DMF the membrane was exposed for 30 minutes to 2,0 mL of 0.3 M side chain protected N—Fmoc—Glu—O—Pfp, 0.3 M HOBT in dry DMF at room temperature. The membrane was subsequently washed with DMF. The cycle of washing, deprotection, washing and coupling was repeated using the various N—Fmoc O—Pfp esterified amino acids such that the desired sequence N—Fmoc—Ala—Asn—Lys(Boc)—Gly—Phe—Leu—Glu(OBut)—Glu(O—But)—Val (prothrombin precursor) could be achieved. The final N-terminal Fmoc group was removed prior to cleavage of material from the support with trifluoroacetic acid. The material was analyzed by reverse phase hplc after concentration of the acidic solution. The result is shown in FIG. 4. Material in the major peak eluted from the column at the same position as the identical peptide synthesized on a Kieselguhr-polyacrylamide support (E. Atherton, E. Brown, R. C. Sheppard & A. Rosevear, *J Chem. Soc. Chem. Comm.*, page 37, 1981).

Figure 5:
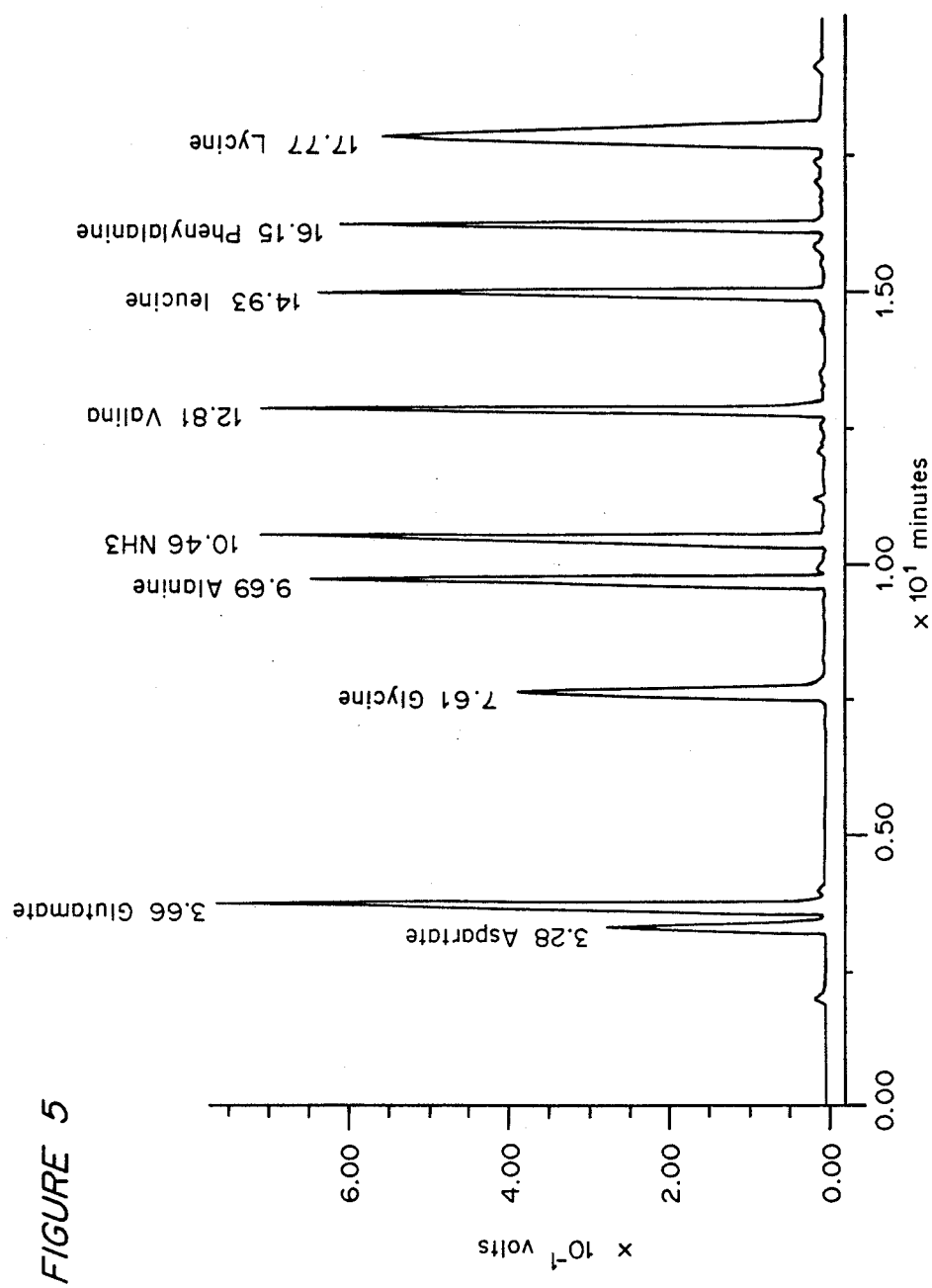
FIG. 5 shows an hplc chromatogram of the hydrolyzed nonapeptide in the form of PTC derivitized amino acids.

FIG. 5 shows an hplc chromatogram of the PTC amino acids obtained after hydrolysis of the peptide and subsequent derivitization with phenylthioisocynate according to standard procedures, indicating the correct amino acid composition. The amino acid sequence was confirmed by the solid phase Edman degradation procedure.

EXAMPLE 8

Synthesis of Oligonucleotides on Polypropylene Membranes

A polypropylene membrane (0.180 g) grafted with polyethoxyethyl acrylate was treated with 2.0 mmol of O-dimethoxy trityl aminoethanol in 2.0 ml of DMF for 19 hrs at 80° C. The membrane was washed with methanol and dried. A small portion of the material was assayed for the presence of the dimethoxytrityl group (see example 2). The assay revealed the polymer contained 0.0022 mmol of protected alcohol functional group per gram of polymer.

A 0.8 cm² disc of the membrane was placed in the specially designed holder of FIG. 1 fitted in a MilliGen 6500 DNA Synthesizer. The synthesis of d(T—C—C—C—A—G—T—C—G—A—C—G—T)

was conducted using a standard phosphoramidite synthesis protocol (Sinha et al. supra). At the conclusion of the synthesis, the disc was treated with 0.3 ml of concentrated aqueous ammonia for 12 hours at 55° C. Acid hydrolysis of the 5' terminal dimethoxytrityl group indicated 0.0003 mmol of oligonucleotides per gram of dry membrane. This indicated an overall step-wise yield of 88%.

Scheme I

-continued

Scheme II

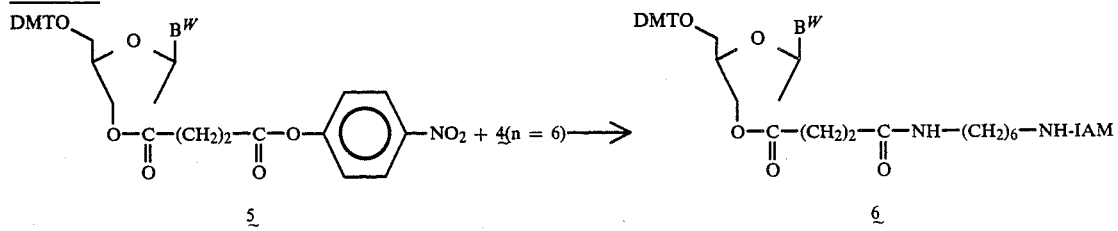

Scheme III

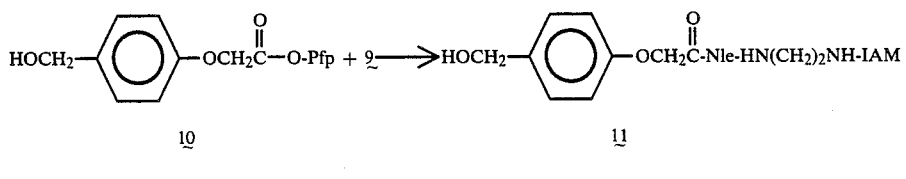

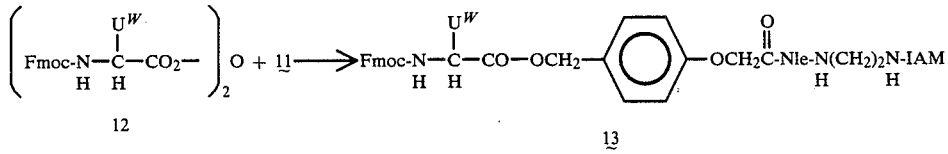

Scheme IV

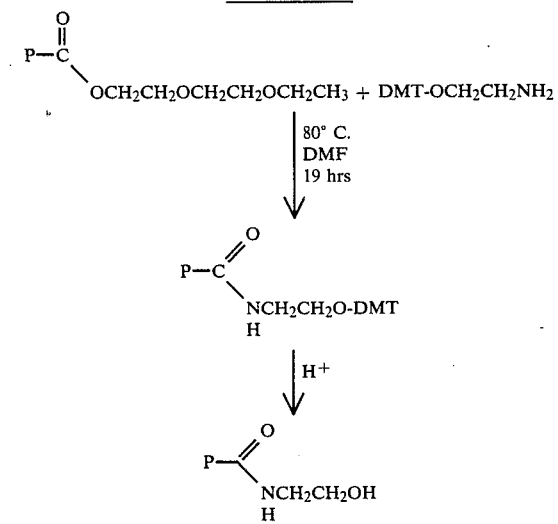

Equivalents

Those skilled in the art will recognize, or be able to ascertain, with no more than routine experimentation, many equivalents to the specific embodiments of the invention described herein. These equivalents are intended to be encompassed by the following claims.

We claim:

1. A modified membrane comprising a polymeric membrane having a protected nucleoside or amino acid linked thereto.

2. A modified membrane represented by the formula:

$$P-X-Y-N-Z-S^W$$

wherein

P is a polymeric membrane;

X is a functional group on the membrane;

Y—N—Z is a linker wherein N is a spacer molecule and Y and Z are the same or different functional groups, the linker being bound to the membrane through its functional group Y to the functional group X; and $S^W$ is a protected nucleoside or amino acid, $S^W$ being bound to the linker through the functional group Z of the linker.

3. A modified membrane of claim 2, wherein the membrane P comprises a flat, permeable polymeric material of porous structure which contains functional groups within its constituent monomeric units for attachment of the spacer group.

4. A modified membrane of claim 3, wherein the monomers are acrylic or methacrylic acid esters having a free alcohol or ester function for attachment of the spacer group.

5. A modified membrane of claim 3, wherein the polymeric material is a cross-linked polymer selected from the group consisting of polydialkylsilandiols, polydialkylsiloxanes, polyvinyl alcohols, polyoxymethylenes and polyoxyethylenes.

6. A modified membrane of claim 2, wherein the membrane is a flat, permeable, polymeric material having a porous structure wherein a functional group for attachment of the spacer has been introduced.

7. A modified membrane of claim 6, wherein the polymeric material comprises polystyrenes, polysulfones containing aromatic residues, polyesters, polyamides, polycarbonates, polyvinylidene difluoride and polyvinyl acetate.

8. A modified membrane of claim 2, wherein the membrane is a flat, permeable, polymeric material having a porous structure onto which are grafted moieties containing functional groups.

9. A modified membrane of claim 8, wherein the polymeric material comprises polysulfones, polytetrafluoroethylene, polyethylene, polypropylene or polyvinyllidene difluoride.

10. A modified membrane of claim 2, wherein the membrane is a flat, permeable, polymeric material having a porous structure onto which is coated a second polymeric material containing free functional groups for attachment of the spacer.

11. A modified membrane of claim 10, wherein the polymeric material comprises polysulfones, polytetrafluoroethylene, polyethylene, polypropylene or polyvinylidene difluoride.

12. A modified membrane of claim 10, wherein the second polymeric material comprises acrylic or methacrylic acid esters having a free alcohol or ester function for attachment of the spacer group.

13. A modified membrane of claim 2 wherein N is —$(CH_2)_n$—, where n is 1–20.

14. A modified membrane of claim 2 wherein N is —NH—$(CH_2)_m$—NHCO—$(CH_2)_m$—CO—, where m is 1–6.

15. A modified membrane of claim 2 wherein N is oligoglycine.

16. A modified membrane of claim 2 wherein Y and Z are individually selected from the group consisting of

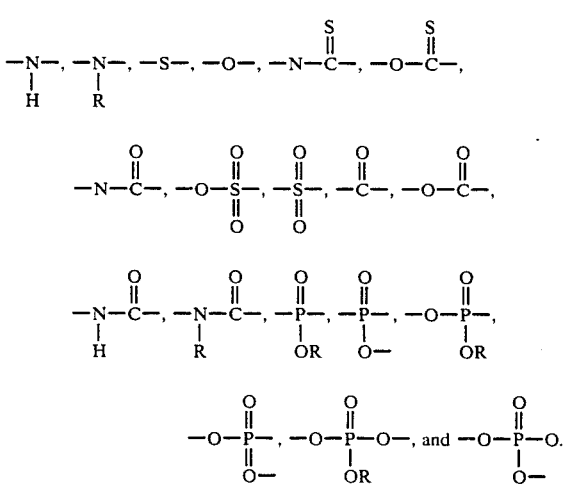

17. A modified membrane of claim 2 wherein $S^W$ represents a nucleoside of the formula:

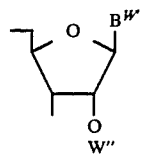

wherein $B^W$ is a nucleoside base having a protecting group for protection of exocyclic amino groups; and W″ is a H or a protecting group for the 2′ hydroxy group.

18. A modified membrane of claim 17 wherein W″ is a trityl group, an acyl group or a silyl group.

19. A modified membrane of claim 2 wherein $S^W$ represents an amino acid of the formula:

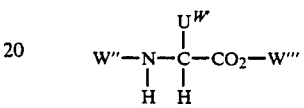

wherein U represents an amino acid side chain; W′ represents protecting groups for the side chain of the amino acid; W″ represents a protecting group for the amino group of the amino acid; W‴ represents a protecting group for the carboxy group of the amino acid.

20. A modified membrane of claim 19 wherein $S^W$ is norleucine attached to the linker through its carboxyl group.

21. A modified membrane of claim 20, wherein the primary amino group of the nucleocine is protected with fluoroenyl-methyloxycarbonyl.

22. A method of synthesizing an oligonucleotide comprising sequentially coupling nucleotide to a modified membrane of claim 17.

23. A method of synthesizing a peptide comprising sequentially coupling amino acids to a modified membrane of claim 19.

24. A method of synthesizing an oligonucleotide comprising the steps of:

a. providing a modified membrane represented by the formula:

$$P—X—Y—N—Z—S^W$$

wherein
P is a polymeric membrane;
X is a functional group on the membrane;
Y—N—Z is a linker wherein N is a spacer molecule and Y and Z are the same or different functional groups, the linker being bound to the membrane through the functional group X; and
$S^W$ is a protected nucleoside, $S^W$ being bound to the linker through the functional group Z of the linker;

b. coupling a nucleoside phosphoramidite to the nucleoside $S^W$ to produce a membrane-bound nucleoside-nucleotide having a phosphite triester linkage;

c. oxidizing the phosphite triester to form a phosphate triester linkage; and d. sequentially coupling additional nucleoside phosphoramidites to the membrane-bound nucleoside-nucleotide, and after each coupling step, oxidizing the resulting phosphite triester linkage to a phosphate triester to produce a membrane-bound polynucleotide.

25. A method of claim 24, wherein the nucleside phosphoramidite is a nucleoside beta-cyanoethyl phosphoramidite.

26. A method of claim 24, further comprising removing the protecting groups from the membrane bound polynucleotide.

27. A method of claim 26, wherein the synthesized polynucleotide is cleaved from the membrane.

28. A membrane-bound polynucleotide produced by the method of claim 24.

29. A method of synthesizing a peptide, comprising the steps of:
a. providing a modified membrane of the formula $$P—X—Y—N—Z—S^W$$

wherein
P is a polymeric membrane;
X is a functional group on the membrane;
Y—N—Z is a linker wherein N is a spacer molecule and Y and Z are the same or differential functional groups, the linker being bound to the membrane through the functional group X; and
$S^W$ is a amino acid, $S^W$ being bound to the linker through the functional group Z of the linker; and
b. sequentially coupling amino acids to $S^W$ to produce a membrane-bound peptide.

30. A method of claim 29, further comprising the step of removing the protecting groups from the membrane-bound peptide.

31. A method of claim 29, wherein the synthesized peptide is cleaved from the membrane.

32. A membrane-bound peptide produced by the method of claim 29.

33. A method of claim 29, wherein $S^W$ represents a norleucine.

34. A method of claim 29, wherein a second linker group is attached to $S^W$, the linker group providing an functional group for coupling of subsequent protected amino acids.

35. A method of claim 34, wherein the linker is p-hydroxymethylphenoxyacetic acid.

36. A membrane having an oligonucleotide attached through a terminus of the oligonucleotide.

37. A membrane having an peptide attached through a terminus of the peptide.

38. A membrane having an attached oligonucleotide or peptide represented by the formula:

$$P—X—Y—N—Z—(—S^W)_n$$

wherein
P is a polymeric membrane;
X is a functional group on the membrane;
Y—N—Z is a linker wherein N is a spacer molecule and Y and Z are the same or different functional groups, the linker being bound to the membrane through the functional group X; and
$(S^W)_n$ represents an oligonucleotide or peptide comprised of protected or partly protected nucleotides or amino acids, wherein n is the number of nucleotide or amino acid units of the oligonucleotide,
$(S^W)_n$ being bound to the linker through the functional group Z of the linker.

39. A membrane having an attached oligonucleotide or peptide represented by the formula:

$$P—X—Y—N—Z—(—S)_n$$

wherein
P is a polymeric membrane;
X is a functional group on the membrane;
Y—N—Z is a linker wherein N is a spacer molecule and Y and Z are the same or different functional groups, the linker being bound to the membrane through the functional group X; and
$(S)_n$ represents an oligonucleotide or peptide, wherein n is the number of nucleotide or amino acid units of the oligonucleotide or peptide, $(S)_n$ being bound to the linker through the functional group Z of the linker.

40. A modified membrane of the formula:

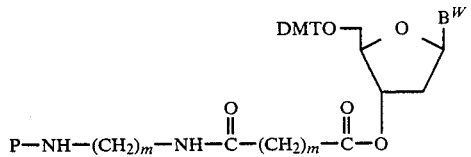

wherein
P is a polyvinylidene difluoride;
m is 1 through 6;
$B^W$ is a nucleoside base having a protecting group for protection of exocylic amino groups; and
DMT is the 4,4-dimethoxytrityl protecting group.

41. A modified membrane of the formula:

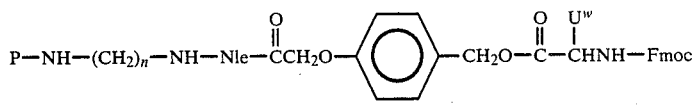

wherein
P is a membrane comprising polypropylene coated with hydroxyporpylacrylate;
n=1–20;
Nle is norleucine;
$U^W$ is an amino acid side chain; and
Fmoc is a fluorenylmethoxycarbonyl protecting group.

42. A modified membrane of claim 33, wherein an amino acid is linked to norleucine by ester linkage with a benzyl alcoholic linker.

* * * * *

UNITED STATES PATENT AND TRADEMARK OFFICE
CERTIFICATE OF CORRECTION

PATENT NO. : 4,923,901

DATED : May 8, 1990

INVENTOR(S) : Hubert Koester and James M. Coull

It is certified that error appears in the above-identified patent and that said Letters Patent is hereby corrected as shown below:

In Column 13, Example 8, delete "Scheme II" and insert

--- Scheme II

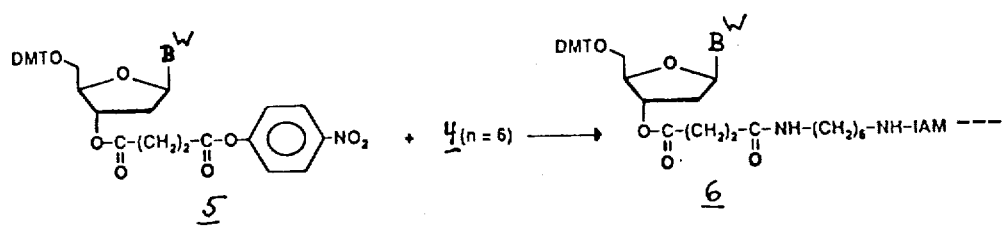

Signed and Sealed this

Sixteenth Day of February, 1993

*Attest:*

STEPHEN G. KUNIN

*Attesting Officer*   *Acting Commissioner of Patents and Trademarks*